United States Patent
Rayner et al.

(10) Patent No.: US 7,410,946 B2
(45) Date of Patent: Aug. 12, 2008

(54) METHOD FOR TREATING DAMAGE IN INTACT SKIN COMPRISING ADMINISTERING A COMPOSITION COMPRISING BASIC MILK GROWTH FACTORS IN AMOUNTS HIGHER THAN THOSE IN MILK

(75) Inventors: Timothy Edward Rayner, Netherby (AU); Allison June Cowin, Beaumont (AU); David Andrew Belford, Seacliff Park (AU)

(73) Assignee: Novozymes Biopharma Au Limited, Thebarton (AU)

( * ) Notice: Subject to any disclaimer, the term of this patent is extended or adjusted under 35 U.S.C. 154(b) by 55 days.

(21) Appl. No.: 10/332,705

(22) PCT Filed: Jul. 13, 2001

(86) PCT No.: PCT/AU01/00854

§ 371 (c)(1),
(2), (4) Date: Mar. 7, 2003

(87) PCT Pub. No.: WO02/05828

PCT Pub. Date: Jan. 24, 2002

(65) Prior Publication Data

US 2004/0081673 A1    Apr. 29, 2004

(30) Foreign Application Priority Data

Jul. 13, 2000    (AU) .................... PQ8786

(51) Int. Cl.
*A61K 35/20* (2006.01)
*A61K 38/17* (2006.01)
(52) U.S. Cl. ..................... 514/12; 424/535
(58) Field of Classification Search ........... 424/535, 424/401, 59; 530/832; 514/12
See application file for complete search history.

(56) References Cited

U.S. PATENT DOCUMENTS

| 3,959,491 | A  | * | 5/1976  | Young et al. ............... 514/775 |
| 5,435,997 | A  | * | 7/1995  | Burns ......................... 424/73 |
| 5,750,149 | A  | * | 5/1998  | Gobbi ........................ 424/535 |
| 5,866,418 | A  | * | 2/1999  | Ballard et al. ............... 435/384 |
| 6,177,550 | B1 |   | 1/2001  | Meyer et al. |
| 6,194,208 | B1 | * | 2/2001  | Belford et al. .............. 435/391 |
| 6,319,522 | B1 | * | 11/2001 | Ballard et al. ............... 424/535 |

FOREIGN PATENT DOCUMENTS

DE    19649891 A1    6/1998

(Continued)

OTHER PUBLICATIONS

Oishi, Hifumi et al, Patent Gazette, No. 8-133943, May 28, 1996 (English Abstract pp. 1-6).

(Continued)

*Primary Examiner*—Rebecca Prouty
*Assistant Examiner*—Rosanne Kosson
(74) *Attorney, Agent, or Firm*—Birch, Stewart, Kolasch & Birch, LLP

(57) ABSTRACT

This invention relates to a method for treating skin damage, comprising the step of administration of a pharmaceutical or dermatological composition of basic milk factors to the area of the skin of a subject in need of such treatment. The invention further relates to a method for cosmetically treating the aged appearance of skin. The skin damage may be the result of normal biological ageing, environmental factors, dermatological disorders, medical treatments, surgical treatments and/or medical conditions. The aged appearance of skin may be attributed to wrinkles, blemishes, sagging, hyperpigmentation, changes to skin thickness and/or a rough appearance. In a preferred embodiment, the subject in need of such treatment requires the enhancement of the youthful appearance of their skin. The invention further relates to compositions for the treated of these conditions.

7 Claims, 11 Drawing Sheets

The penetration of topically formulated BMF-1 in living skin. Integrated Optical Density representation.

| | FOREIGN PATENT DOCUMENTS | | |
|----|----|----|----|
| ES | 2 139 525 A1 | 1/2000 |
| FR | 2 781 151 A1 | 2/2000 |
| WO | WO 92/00994 A | 1/1992 |
| WO | WO 9200994 A1 * | 1/1992 |
| WO | WO 95/29933 A | 11/1995 |
| WO | WO 96/34614 A1 | 7/1996 |
| WO | WO 97/34929 A1 | 9/1997 |

OTHER PUBLICATIONS

Rayner, Timothy E. et al., American Journal of Physiology, vol. 278, No. 6, Part 2, pp. R1651-R1660 (Jun. 2000).

Francis, G. L. et al., Journal of Dairy Science, American Dairy Science Association, vol. 78, No. 6, pp. 1209-1218 (Jun. 1995).

* cited by examiner

BMF-1 and BMF-2 stimulates proliferation of human keratinocytes.

BMF-1 stimulates collagen production by human skin fibroblasts.

The penetration of topically formulated BMF-1 in living skin. Micrograph representation.

The penetration of topically formulated BMF-1 in living skin. Integrated Optical Density representation.

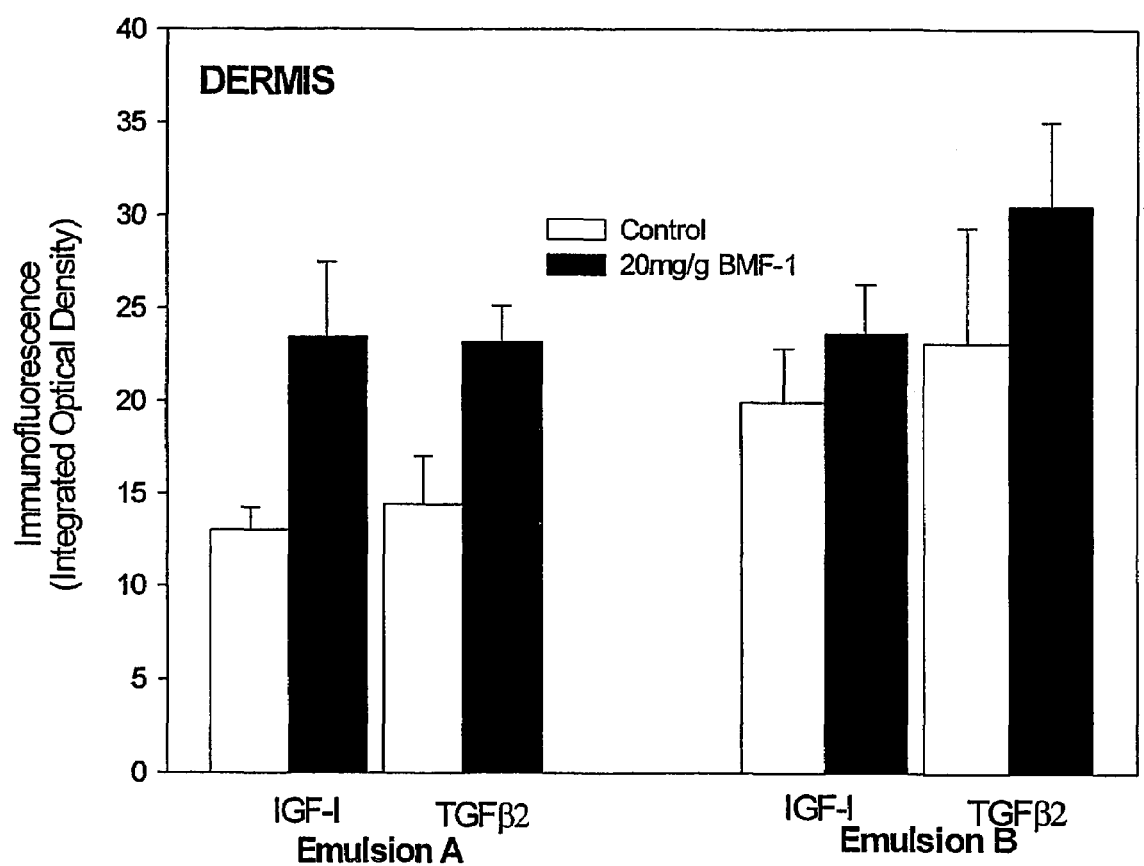
Figure 3B(ii)
The penetration of topically formulated BMF-1 in living skin. Integrated Optical Density representation.

Topically formulated BMF-1 increases dermal cellularity in living skin after repeated application for 4 weeks.

Topically formulated BMF-1 increases dermal collagen type III deposition in living skin.

BMF-1 product stimulates collagen mRNA synthesis and inhibits matrix-metalloproteinase 1 (MMP-1) mRNA synthesis by human skin fibroblast cells. Micrograph representation.

BMF-1 product stimulates collagen mRNA synthesis and inhibits matrix-metalloproteinase 1 (MMP-1) mRNA synthesis by human skin fibroblast cells. Graphical representation.

BMF-1 and BMF-2 product stimulate collagen mRNA synthesis by human skin fibroblast cells. Micrograph representation.

BMF-1 and BMF-2 product stimulate collagen mRNA synthesis by human skin fibroblast cells. Graphical representation.

METHOD FOR TREATING DAMAGE IN INTACT SKIN COMPRISING ADMINISTERING A COMPOSITION COMPRISING BASIC MILK GROWTH FACTORS IN AMOUNTS HIGHER THAN THOSE IN MILK

This application is the national phase under 35 U.S.C. §371 of PCT International Application No. PCT/AU01/00854 which has an International filing date of Jul. 13, 2001, which designated the United States of America and which claims priority to Australian Provisional Application No. PQ8786, filed Jul. 13, 2000.

This invention relates to compositions and methods for treating and preventing skin damage. The present invention also relates to compositions and methods for improving the cosmetic appearance of skin.

INTRODUCTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

The steady deterioration of the appearance and function of skin with age can be attributed to a combination of genetically determined ageing and the cumulative damage to the skin caused by various environmental factors. A distinction can be drawn between intrinsic ageing (or normal biological ageing), and accelerated or premature ageing as a result of damage induced by environmental factors.

The deterioration of the appearance and function of skin is often associated with skin damage caused by environmental factors such as ultra-violet irradiation resulting from sun exposure, exposure to other environmental pollutants or toxins and dermatological disorders. Damage to the skin by environmental factors serves to aggravate the effects of normal biological ageing, producing more detrimental effects on the function and appearance of the skin. The reduction in the youthful appearance of the skin can also be attributed to the functional and structural deterioration of skin as a result of normal biological ageing, exclusive of environmental factors. Such deterioration can manifest visibly as localised furrows (wrinkles), blemishes, a loss of elasticity of the skin leading to sagging, hyperpigmentation, changes to skin thickness and a dry and rough appearance making the skin more susceptible to mechanical trauma or disease processes leading to blister formation.

The deterioration of the appearance and function of skin is attributed to a number of physiological changes in the cellular and molecular processes of the epidermal and dermal tissue (reviewed by Gilchrest 1996). As skin ages, genetically determined factors and various environmental elements reduce skin epidermal cell (keratinocytes) and dermal cell (fibroblast) proliferation and viability as the cells become senescent reducing the total dermal cellularity. This results in skin having a dull and aged appearance and a marked decrease in the dermal thickness. In addition, the activity of metalloprotease enzymes, including matrix metalloprotease 1, that degrade collagen and other dermal matrix proteins is increased. This further results in the fragmentation of the supportive collagenous framework of the dermal tissue as the rate of collagen (type I and type III) degradation exceeds the rate of collagen production. This leads to a loss of structural support as indicated by wrinkles and sagging, and contributes to enhanced dermal thinning.

A number of agents have been used to prevent and treat intrinsic and environmental damage to skin. These include alpha-hydroxy acids, retinoids (vitamin A and its derivatives such as retinoic acid), copper-peptide complexes, and vitamin C. Two of the most commonly used agents include retinoic acid and alpha-hydroxy acid.

Retinoic acid has been used as an active ingredient in cosmetic formulations claiming anti-ageing effects by reducing the appearance of fine lines, wrinkles and mottled darkened spots and roughness of facial skin. A problem with the use of retinoic acid is that the positive effects of retinoids on skin damage are reversed during long term therapy. This results in the beneficial histological parameters returning to near pre-therapy levels.

Furthermore, retinoic acid has been found to be deficient in eliminating wrinkles, repairing sun induced skin damage and restoring skin to its healthier structure. The use of compositions containing retinoids for the long-term treatment of skin damage can also present significant side effects. A further difficulty is that the incorporation of these agents into suitable carriers is problematic. Retinoic acid has been shown to cause erythema, burning and mild scalding, irritation, and increased sun-sensitivity. It also has been identified as a teratogen, which prevents its use by pregnant women (Gilchrest 1996).

Alpha-hydroxy acids have been reported to also increase skin thickness as well as collagen and elastin synthesis (reviewed by Bergfeld 1997). The changes in the skin reportedly due to the alpha-hydroxy acids however are associated with the corrosive or exfoliative action of these preparations, which induces acute skin damage and results in a primary healing response. Hence these agents create apparent, short-term benefits by stimulating skin renewal due to the damage they cause. Consequently the application of alpha-hydroxy acid to skin can result in significant skin irritation and side effects that mirror those described for retinoic acid (including sun sensitivity). Glycolic acid, perhaps the most commonly used alpha-hydroxy acid, is absorbed through the skin and is potentially toxic to the kidneys and, to a lesser degree, the liver.

More recently, naturally occurring growth factors or cytokines, which are the physiological regulators of intrinsic tissue repair, have been proposed as agents capable of treating wounded skin. Importantly, the processes for healing wounded skin which has lost its structural and functional integrity (including lacerations, penetrations, ulcers and burns) proceeds as a fibroproliferative response leading to the formation of a fibrotic scar. Wound repair is an intricate, temporal process that is dependent on the well described physiological processes of haemostasis, inflammation, wound contraction and re-epithelialisation (Mast 1992). Thus in wound healing, the organ is patched rather than restored (Clark 1995). However, the repair of skin damage which is substantially intact or non-wounded is attributed to a regeneration process and distinct from the processes of wound healing. This can only occur in tissue having its structural and functional integrity maintained, thereby including skin damaged by environmental factors and skin which has lost its youthful appearance.

Hence it is an aspect of the present invention to provide a therapeutic and preventative treatment for skin damage and the aged appearance of skin comprising the administration of basic milk factors. The milk factors can directly increase keratinocyte and fibroblast cell proliferation and viability, increase dermal cellularity whilst stimulating dermal collagen production further resulting in the formation of new loose connective tissue in the dermis.

Accordingly, it is an object of the present invention to overcome or alleviate some of the problems of the prior art, and to provide such treatment.

SUMMARY OF THE INVENTION

In a first aspect, the present invention provides a composition for treating or preventing skin damage, the composition comprising an effective amount of basic milk factors or variants thereof, said basic milk factors comprising a plurality of cell growth stimulating factors having basic to approximately neutral isoelectric points.

The term "treating or preventing" as used herein is intended to include either therapeutic treatment of skin damage, or preventive or prophylactic procedures performed before the occurrence of skin damage. Thus the patient to be treated may already have skin damage, or may be at risk of having skin damage. The term "treating or preventing" is also intended to include either cosmetic treatment to reduce the aged appearance of skin, or preventive cosmetic treatment performed before the occurrence of the aged appearance of skin. Thus the patient to be treated may already have skin with an aged appearance, or may be at risk of having skin with an aged appearance.

The term "treating or preventing" also includes;

1) the regeneration of new epithelial, epidermal and dermal tissue, including the regeneration of keratinocyte and fibroblast cells and the regeneration of collagenous tissue, which adds to the existing epidermal and dermal tissue, and which may serve to replace the epidermal and dermal tissue lost prior to the onset of treatment;

2) the preservation of existing epithelial, epidermal and dermal tissue, including the preservation of keratinocyte and fibroblast cells and the preservation of collagenous tissue, which encompasses epidermal and dermal tissue existing at the onset of treatment and any newly formed epidermal and dermal tissue following onset of treatment;

3) improving the function of the skin;

4) enhancing the youthful appearance of skin, including the enhancement of skin flexibility, firmness, smoothness, suppleness and/or elasticity;

5) reducing wrinkles; and/or 6) reducing blemishes.

It will be appreciated that in the method of the invention, the mammal to be treated may be a human, a domestic animal, a companion animal or a zoo animal.

The term "skin damage" as used herein includes any resultant adverse effect on the skin by way of normal biological ageing, environmental factors, dermatological disorders, medical or surgical treatments, or a combination of any of the above. Adverse effects on the skin may manifest visibly as localised furrows (wrinkles), blemishes, a loss of elasticity of the skin leading to sagging, hyperpigmentation, changes to skin thickness and a dry and rough appearance making the skin more susceptible to mechanical trauma or disease processes leading to blister formation. Also included are adverse effects which are not apparent to the eye. For example deleterious metabolic changes in the skin cells, and changes to skin vascularisation. Such changes include reduced skin epithelial cell, epidermal cell (keratinocyte) and dermal cell (fibroblast) proliferation and viability. Such changes may reduce the total dermal cellularity and cause the fragmentation of the collagenous framework as the rate of collagen (type I and type III) degradation exceeds the rate of collagen production.

The term "basic milk factors" as used herein means a mixture of growth factors concentrated from a milk product having cell proliferating properties, in which the proportions of the salt and/or main protein constituents thereof are altered and the growth factors have approximately neutral to basic isoelectric points. Basic milk factors may be derived from cheese whey, colostral whey, skim milk or acid whey. Examples of basic milk factors include concentrates of milk products subject to organic solvent extraction, ultrafiltrates of milk products or milk products subjected to adsorption and to elution from chromatography matrices. Methods for the preparation of basic milk factors from milk products are well known in the art and can be addressed with no more than routine experimentation.

Importantly, since the inventors have surprisingly demonstrated that a growth factor composition having basic to approximately neutral isoelectric points, obtained from a milk product has the capacity to effectively pass through the uppermost layers of the skin as shown by the translocation of insulin-like growth factor I (IGF-I) and transforming growth factor beta 2 (TGFβ2), resulting in the growth factors exerting their biological effects on competent cells leading to metabolic changes in those cells, persons skilled in the art will readily be able to use other alternative and suitable growth factor compositions obtained from milk products to obtain the said affect requiring no more than mere routine experimentation.

In a second aspect the present invention provides a composition for cosmetically treating or preventing the aged appearance of skin, the composition comprising an effective amount of basic milk factors or variants thereof, said basic milk factors comprising a plurality of cell growth stimulating factors having basic to approximately neutral isoelectric points.

The term "effective amount" as used herein means that amount necessary to at least partially attain the desired effect, or to delay the onset of, inhibit the progression of, or halt altogether, the onset or progression of skin damage. Such amounts may depend, of course, on the particular condition being treated, the severity of the condition and individual parameters, including age, physical condition, size, weight and other concurrent treatments. These factors are well known to those of ordinary skill in the art, and can be addressed with no more than routine experimentation. It is generally preferred that a minimum effective dose be determined according to sound medical or therapeutic judgement. It will be understood by those of ordinary skill in the art, however, that a higher dose may be administered for medical or other reasons.

The term "effective amount" as used herein also means that amount necessary to at least partially attain a desired cosmetic effect, or to delay the onset of, or inhibit the progression of the appearance of aged skin. Such amounts may depend, of course, on the particular condition being treated, the severity of the condition and individual parameters, including age, physical condition, size, weight and other concurrent treatments. These factors are well known to those of ordinary skill in the art, and may be addressed with no more than routine experimentation. It is generally preferred that a minimum effective dose be determined according to cosmetic judgment.

Preferably, the skin to be treated is substantially intact. The term "substantially intact" as used herein refers to skin which has maintained structural and functional integrity and barrier function. Examples of intact skin include skin showing (or having the potential to show) signs of normal biological ageing, or skin damaged (or having the potential to be damaged) by environmental exposure whereby the skin repairs by regeneration processes. Also included is skin which has been subjected to medical or surgical treatment, where the skin is left substantially intact. Intact skin does not include wounded skin, thereby excluding lacerations, penetrations, ulcers and burns.

The repair of damaged intact or non-wounded skin is attributed to a regeneration process. This can only occur in tissue having structural and functional integrity maintained, thereby including skin damaged by environmental factors and ageing. This situation is distinguished from the healing of wounded skin, which has lost its structural and functional integrity (including lacerations, penetrations, ulcers and burns) that proceeds as a fibroproliferative response which develops into a fibrotic scar. Thus in wound healing, the organ is patched rather than restored. However, the processes of wound healing are distinct from those of repair of damaged intact skin, which repairs by a regeneration process.

In a preferred form of the invention the basic milk factors are capable of stimulating proliferation of rat L6 myoblasts.

Preferably the basic milk factors are prepared by subjecting a milk product to cationic exchange chromatography. The cationic exchange resin may be suitable for adsorbing basic proteins such that the more basic components of the milk product are adsorbed thereon. Proteins may be eluted, from the cationic exchange resin with a suitable buffer solution of a sufficiently high ionic strength (e.g. a molarity above 0.2M). The eluate may be filtered to remove salt or any other low molecular weight contaminants.

The cation exchange resin may be a cationic exchange resin suitable for adsorbing a plurality of cell growth stimulating factors. Unsuitable cationic exchange resins include resins with a pore size too small to permit the binding of basic milk proteins. For example the DOWEX AG 50W 2X 50-100 mesh resin would be unsuitable to adsorb a plurality of basic milk factors. A suitable cationic exchange resin used in accordance to the invention includes an agarose-based cationic exchange resin.

The term "milk product" as used herein refers to a derivative from human or animal milk in which the proportions of fat and/or protein constitutes thereof are altered. Examples of milk products include milk whey, skim milk, colostral whey, cheese whey and acid (casein) whey.

Preferably the milk product is selected from the group comprising milk whey, skim milk, colostral whey, cheese whey and acid whey. The basic milk factors may be obtained from cheese whey wherein the proportions of the main protein constituents thereof are altered.

More preferably the milk product is derived from an ungulate mammal. Importantly, epidermal growth factor (EGF) has not been shown to be present in milk of an ungulate mammal.

In a preferred form of the invention the basic milk factors are BMF-1 and/or BMF-2. A method for preparing BMF-1 is described in Australian Patent 645589, the entire disclosure of which is incorporated herein by reference.

A method for preparing BMF-2 is described in Australian Patent 702002, the entire disclosure of which is incorporated herein by reference. In this process the basic milk factors may be modified to enhance activity, by transient acidification and/or purification under acidic conditions, for example using molecular sieve chromatography or controlled pore ultrafiltration. Accordingly, BMF-2 may include a plurality of modified milk growth factors having isoelectric points above approximately 6.0 and molecular weights in the range of approximately 5000 to 30,000, the basic milk factors being modified by transient acidification.

Preferably, the basic milk factors include growth stimulating factors selected from the group comprising insulin-like growth factor I (IGF-I), insulin-like growth factor II (IGF-II), platelet derived growth factor (PDGF), fibroblast growth factor (FGF) and Transforming Growth Factor Beta (TGFβ). These growth factors have basic to approximately neutral isoelectric points ie between approximately 6.0 and approximately 10.5.

Preferably, the growth factors present in the composition are deficient in EGF.

Preferably the concentration of the basic milk factors is from 1 μg/mg to 500 mg/g. More preferably the concentration of the basic milk factors is from 0.01 mg/g to 200 mg/g.

The preparations contemplated by the present invention include any formulations suitable for the cutaneous application of basic milk factors. Suitable carriers and/or diluents are known to those skilled in the art and include conventional solvents, dispersion media, fillers, aqueous solutions, sunscreens, antibacterial and antifungal agents, or absorption-promoting agents, either alone or in combination.

Supplementary active ingredients may also be incorporated into the compositions, such as additional growth factors, Vitamin A, C and E, dimethylsulfoxide, retinoic acid, copper-peptide complexes, alpha-keto acids, lanolin, vaseline, aloe vera, methyl or propyl paraben, either alone or in combination.

The additional growth factors may be added to enhance activity of the composition. The growth factors may be selected from the group comprising IGF-I, IGF-II, PDGF, FGF, TGFβ and keratinocyte growth factor (KGF).

Preferably the composition comprises an effective amount of basic milk factors effective to alleviate or prevent the signs and/or symptoms of skin damage.

Preferably, the composition comprises an effective amount of basic milk factors effective to inhibit the progression of, or halt altogether, the onset or progression of the skin damage.

In a preferred form, the skin to be treated is substantially intact.

The composition may be in a form selected from the group comprising cosmetically acceptable liquids, creams, oils, lotions, ointments, gels, roll-on liquids, skin patches, sprays, glass bead dressings, synthetic polymer dressings impregnated with basic milk factors, solids, conventional cosmetic night creams, foundation creams, suntan lotions, hand lotions, insect repellents, make-up, make-up bases and masks. Except insofar as any conventional medium or agent is incompatible with the active ingredient, use thereof in the cosmetic compositions of the present invention is contemplated.

Methods and carriers for the preparation of pharmaceutical and cosmetic compositions are well known in the art, as set out in textbooks such as Remington's Pharmaceutical Sciences, 18$^{th}$ Edition, Mack Publishing Company, Easton, Pa., USA, the contents of which is incorporated herein.

Preferably the composition comprises a cosmetically effective amount of basic milk factors. More preferably the composition comprises an effective amount of basic milk factors effective to alleviate or prevent the signs and/or symptoms of the aged appearance of skin. Most preferably the composition comprises an effective amount of basic milk factors effective to inhibit the progression of, or halt altogether, the onset or progression of the aged appearance of skin.

In a preferred form of the invention the skin to be treated is substantially intact.

In another aspect the present invention provides the use of basic milk factors comprising a plurality of cell growth stimulating factors having basic to approximately neutral isoelectric points for the manufacture of a composition for the treatment or prevention of skin damage.

Preferably the treatment alleviates or prevents the signs and/or symptoms of the skin damage. More preferably the treatment inhibits the progression of, or halts altogether, the onset or progression of the skin damage.

In a preferred form, the skin to be treated is substantially intact.

The use may incorporate the compositions as described herein.

In another aspect the present invention provides the use of basic milk factors comprising a plurality of cell growth stimulating factors having basic to approximately neutral isoelectric points for the manufacture of a composition for cosmetic treatment or prevention of the aged appearance of skin.

Preferably the treatment alleviates or prevents the signs and/or symptoms of the aged appearance of skin. More preferably the treatment inhibits the progression of, or halts altogether, the onset or progression of the aged appearance of skin.

The use may incorporate the compositions as described herein.

In a preferred form the skin to be treated is substantially intact.

In another aspect the present invention provides a method for treating or preventing skin damage comprising administering to the skin the compositions as described herein. The treating or preventing may alleviate or prevent the signs and/or symptoms of the skin damage. The treating or preventing may also inhibit the progression of, or halt altogether, the onset or progression of the skin damage.

Preferably the skin to be treated is substantially intact.

Preferably the skin damage is the result of normal biological ageing, an environmental factor, a dermatological disorder, medical treatment, surgical treatment or a medical condition, either alone or in combination.

The normal biological ageing may be predetermined by genetic factors. The environmental factor may be poor food hygiene, exposure to a toxin, exposure to a pollutant, sun exposure, ionizing radiation, X-rays, UV-rays, tobacco use, alcohol or stress.

The dermatological disorder may arise from acneic conditions, acne vulgaris, acne rosacea, actinic keratoses, actinodermatoses, angiomas, argyia, chloasma, Darier's disease, dyschromias, lentigines, melasma, nevi, radiodermatitis, rhinophyma, rhytes and rhytides, sebaceous adenomas, sebaceous cysts, seborrheic keratoses, superficial basal cell carcinoma, telangiectasis and/or trichoepitheliomas (Orentreich et al., 2001).

Skin damage may also result from the administration of medications for the management of medical conditions. Preferably the medical treatment is topical glucocorticoid treatment or hemodialysis treatment.

Skin damage may also result from a medical condition including congenital ectodermal dysplasia, diabetes, HIV infection, an infection associated with AIDS, a nutritional deficiency, renal disease, menopause, recessive dystrophic epidermolysis bullosa, Ehlers Danlos syndrome, generalised cutaneous atrophy, localised cutaneous atrophy, scarring alopaecia, pyoderma gangrenosum, or a hormonal alteration, either alone or in combination.

Skin damage may also result from surgical treatments such as liposuction, subscision, electrodesiccation and laser therapy. While these treatments are surgical in nature, such procedures leave the surface of the skin substantially intact, though the dermal structures underneath the intact skin may still be damaged and require treatment.

Preferably the composition is administered topically. More preferably the composition is administered topically at a rate of 0.1 mg/cm$^2$ of skin to 2 g/cm$^2$ of skin.

It is contemplated that the composition may be administered topically by any means which delivers an amount of basic milk factors at the skin tissue to attain the desired therapeutic or cosmetic affect. The composition may be applied to the affected area of the skin of the patient. The frequency of application will depend on the individual circumstances. For example, the composition may be applied daily, or twice daily, or even more frequently.

In another aspect the present invention provides a method for cosmetically treating the aged appearance of skin comprising administering a composition as described herein. The method may alleviate or prevent the signs and/or symptoms of the aged appearance of skin. The method may also inhibit the progression of, or halt altogether, the onset or progression of the aged appearance of skin.

Preferably, the skin to be treated is substantially intact.

In a preferred form of the invention the aged appearance of skin is the result of a wrinkle, a blemish, hyperpigmentation, a change in skin thickness, dryness, or a rough appearance, either alone or in combination.

Preferably the mammal requires the enhancement of the youthful appearance of their skin.

Preferably the composition is administered topically. More preferably the composition is administered topically at a rate of 0.1 mg/cm$^2$ of skin to 2 g/cm$^2$ of skin.

In another aspect the present invention provides a kit for the treatment or prevention of skin damage comprising a composition as described herein in; and instructions for use of the composition in a method as described herein.

In another aspect the present invention provides a kit for cosmetic treatment of the aged appearance of skin, comprising a composition as described herein; and instructions for use of the composition in a method as described herein.

For the purposes of this specification it will be clearly understood that the word "comprising" means "including but not limited to", and that the word "comprises" has a corresponding meaning.

DESCRIPTION OF FIGURES

All data presented is represented as the mean±standard error of the mean.

DETAILED DESCRIPTION OF THE INVENTION

Figure 1:
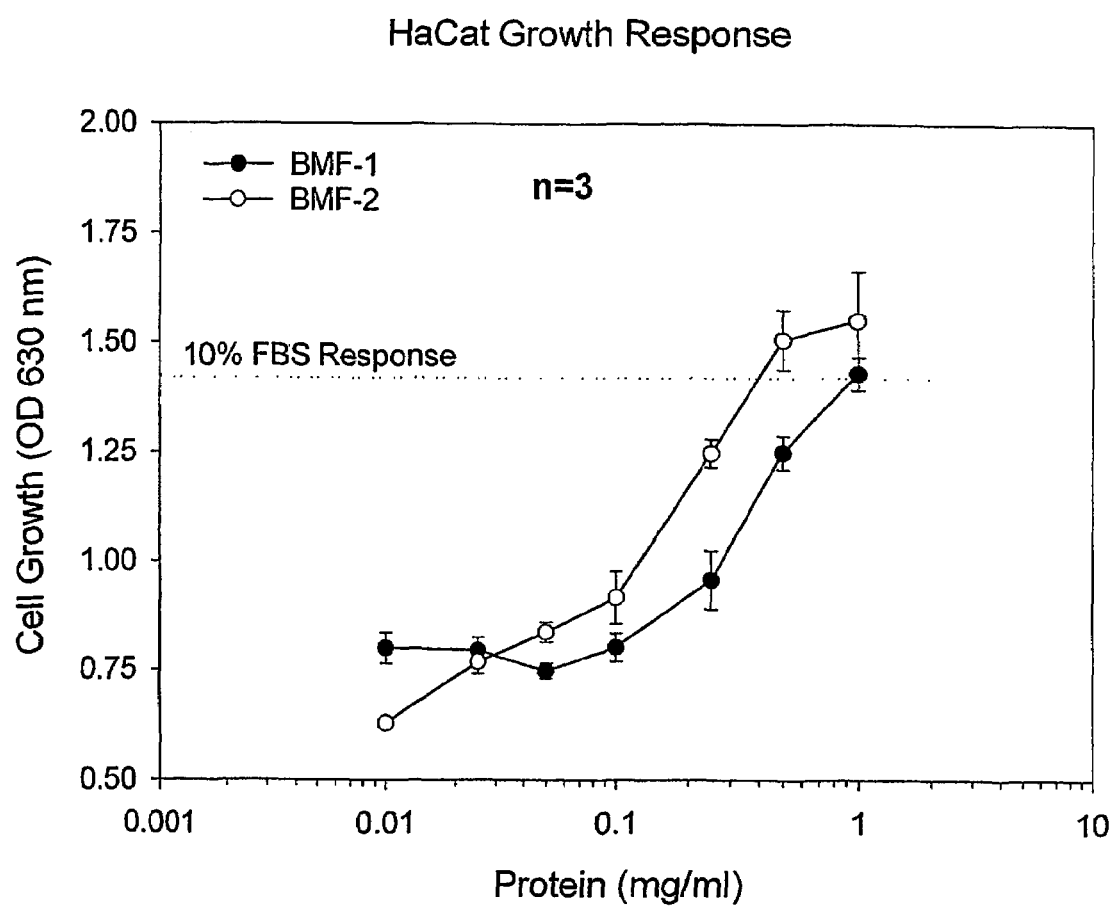
FIG. 1 shows a graph demonstrating the in vitro stimulation of human keratinocyte (HaCat) cells using increasing concentrations of BMF-1 and BMF-2. Cell growth was monitored by measuring the optical density (OD) at a wavelength of 630 nm. The dotted line represents a response that was obtained when cells were treated with 10% foetal bovine serum.

The present invention will now be more fully described with reference to the accompanying non-limiting examples. It should be understood that the following description is illustrative only, and should not be taken in any way as a restriction on the generality of the invention.

EXAMPLE 1

Production of BMF-1 Suitable for the Cosmetic and Therapeutic Treatment of Skin Damage and the Aged Appearance of Skin BMF-1 was prepared as in Australian Patent Number 645589. The process involves the microfiltration of pasteurised whey to remove solids, adsorption of growth-promoting material to a column of S-Sepharose Fast Flow S™ cation exchange resin (Pharmacia) that had been equilibrated with 50 mM sodium citrate buffer to remove unadsorbed material, elution of BMF-1 with 0.4M NaCl added to 10 mM sodium citrate pH 6.5, diafiltration against water and concentration. The composition can be left in liquid form or freeze dried for further formulation.

EXAMPLE 2

Production of BMF-2 Suitable for the Cosmetic and Therapeutic Treatment of Skin Damage and the Aged Appearance of Skin BMF-2 was prepared as in Australian Patent Number 702002. A 10 g sample of BMF-1 prepared as in Example 1 was dissolved in 150 mM PBS and added to 250 mls of 10 mM HCl containing 0.2M NaCl, and the pH adjusted to 2.5 with NaOH. A 2 liter Cellufine GL 1000™ (Amicon) column was equilibrated with a 10 mM solution of HCl containing 0.2M NaCl adjusted to pH 2.5 with NaOH and 125 ml of the dissolved BMF-1 was applied to the column and eluted at 6.8 ml/min with the same solution. 675 ml was collected from when the absorbance profile at 280 nm fell below 0.4 A. This pool was diafiltered against 0.1M ammonium bicarbonate. The composition can be left in liquid form or freeze dried for further formulation.

EXAMPLE 3

Formulations Suitable for Applying Basic Milk Factors to Skin

All units for ingredients of the compositions are measured in "parts". Basic milk factors quantity specified hereby referred to as "qs".

| (i) Cetomacrogol Cream | |
| --- | --- |
| Basic milk factors | qs |
| Cetomacrogol emulsifying wax | 15 |
| Liquid paraffin (by weight) | 10 |
| Chlorocresol | 0.1 |
| Propylene glycol | 5 |
| Distilled water to | 100 |

Cetomacrogol emulsifying wax was melted with paraffin at about 70° C. Chlorocresol and propylene glycol were dissolved in about 50 parts of the distilled water warmed to about the same temperature. After mixing, the composition was adjusted to weight and stirred until cool. Basic milk factors are then added to an appropriate concentration, and mixed thoroughly.

| (ii) Aqueous Cream APF | |
|---|---|
| Basic milk factors | qs |
| Emulsifying ointment | 30 |
| Glycerol | 5 |
| Phenoxyethanol | 1 |
| Distilled water to | 100 |

The emulsifying ointment was melted at about 70° C. The phenoxyethanol was dissolved in the distilled water, warmed to about the same temperature. The composition was mixed, adjusted to weight and stirred until cool. The basic milk factors are then added while stirring thoroughly.

| (iii) Buffered Cream BPC 73 | |
|---|---|
| Basic milk factors | qs |
| Citric acid | 5 |
| Sodium phosphate | 25 |
| Chlorocresol | 1 |
| Emulsifying ointment | 300 |
| Distilled water | 669 |

Emulsifying ointment was melted with the aid of gentle heat, followed by addition of sodium phosphate, citric acid and chlorocresol, previously dissolved in the distilled water at the same temperature. The composition was stirred gently until cold. The basic milk factors are then added and mixed thoroughly.

| (iv) Emulsifying Ointment APF | |
|---|---|
| Basic milk factors | qs |
| Emulsifying wax | 30 |
| White soft paraffin | 50 |
| Liquid paraffin (by weight) | 20 |

The waxes and paraffins were melted together and stirred until cool. Basic milk factors are then added to an appropriate concentration in a portion of the base, gradually incorporating the remainder, followed by thorough mixing.

| (v) Peptide Ointment (as in Neomycin and Bacitracin Ointment BPC 73) | |
|---|---|
| Basic milk factors | qs |
| Liquid paraffin | 10 |
| White soft paraffin to | 100 |

White soft paraffin was melted, and the liquid paraffin incorporated. The mixture was stirred until cold. The basic milk factors are titrated with a portion of the base and gradually incorporated into the remainder of the base.

| (vi) Gel (as used in Lignocaine and Chlorhexidine Gel APF) | |
|---|---|
| Basic milk factors | qs |
| Tragacanth | 2.5 |
| Glycerol | 25 |
| Distilled water to | 100 |

The tragacanth was mixed with glycerol and most of the distilled water. After bringing to the boil, the mixture was cooled, and the basic milk factors are added. The composition was adjusted to weight and mixed well. The finished product was protected from light.

| (vii) Spray (as used in Adrenaline and Atropine Spray BPC 73) | |
|---|---|
| Basic milk factors | qs |
| Sodium metabisulphite | 1 |
| Chlorbutol | 5 |
| Prophylene glycol | 50 |
| Distilled water to | 1000 |

| (viii) Spray (as used in Indospray) | |
|---|---|
| Basic milk factors | qs |
| Alcohol | 95% |

| (ix) Lotions (as used in Aminobenzoic Acid Lotion BPC 73) | |
|---|---|
| Basic milk factors | qs |
| Glycerol | 20 |
| Alcohol 95% | 60 |
| Distilled water to | 100 |

| (x) Cetomacrogol Lotion APF | |
|---|---|
| Basic milk factors | qs |
| Cetomacrogol emulsifying wax | 3 |
| Liquid paraffin | 10 |
| Glycerol | 10 |
| Chlorhexidine gluconate solution | 0.1 |
| Distilled water to | 100 |

Cetomacrogol emulsifying wax was melted with the liquid paraffin at about 60° C. To this mixture, the chlorhexidine solution previously diluted to 50 parts was added, with rapid stirring, with distilled water at the same temperature. After mixing, the composition was adjusted to volume and stirred until cold.

EXAMPLE 4

BMF-1 Increases Proliferation and Viability of Animal Fibroblast Cells

Balb C3T3 mouse fibroblasts were plated into 24-place multiwells 24 hours before treatment to give a monolayer close to confluence. Performed in triplicate, cells were incubated at least overnight in complete growth medium, rinsed with serum-free media then exposed to concentrations of BMF-1 product (1.0 mg/ml) in basal medium (DMEM containing 0.1% FBS) for between 48 and 72 hours.

Cell monolayers were treated with trypsin/EDTA (0.125%/ 0.5 mM) to disperse individual cells. Cells were pelleted, washed in Hanks balanced salt solution (HBSS) and to assess cell number, cells were suspended in 450 µl of HBSS and 50 µl trypan blue and counted manually using a haemocytometer. To assess viability, cells were treated with both annexin V/FITC (1 µg/ml) and propidium iodide (PI, 5 µg/ml) in a total volume of 500 µl at 4° C. for 15 minutes (method modified from Van Engeland et al, 1996).

Flow cytometry was then used to analyse cell viability. Table 1 shows the viability of cultured fibroblasts treated with BMF-1 or basal medium treated with annexin/PI were segregated into the following categories; viable cells (negative annexin V staining and negative PI staining), apoptotic cells (positive annexin staining but negative PI staining) and necrotic cells (positive annexin V staining and positive PI staining).

Table 1 demonstrates that compared to basal DMEM media, BMF-1 (1 mg/ml) stimulated the growth of cultured fibroblasts by approximately 3.0 fold. The percentage of viable cells was increased by 26% in cultures treated with BMF-1 compared with basal medium. BMF-1 also reduced the number of apoptotic and necrotic cells by 73% and 21% respectively compared to basal medium. Thus BMF-1 stimulates the growth and survival of fibroblast cells in culture.

TABLE 1

Effect of BMF-1 (1 mg/ml) on cell growth and survival of cultured fibroblasts (n = 3)

| Treatment | Cell Growth (cells/well × $10^4$) | Annexin/PI (cell viability) | | |
|---|---|---|---|---|
| | | Viable (%) | Apoptotic (%) | Necrotic (%) |
| Basal Medium | 5.5 ± 0.4 | 68.8 ± 1.8 | 21.7 ± 1.0 | 7.0 ± 1.1 |
| BMF-1 | 16.3 ± 1.9 | 86.6 ± 2.2 | 5.9 ± 1.0 | 5.5 ± 1.4 |

EXAMPLE 5

BMF Product Increases Proliferation and Viability of Human Keratinocyte Cells

To assess the effect of BMF-1 and BMF-2 on the growth of human keratinocyte cells (HaCat), cells were plated into 96-well plates to give a monolayer close to confluence. Performed in triplicate, the cells were incubated at least overnight in complete growth medium, starved for at least two hours and then exposed to concentrations of BMF-1 or BMF-2 (0-1.0 mg/ml) dissolved in DMEM for up to 4 days. Replicate wells were exposed to concentrations of 10% FBS to serve as a positive control. Plates were rinsed and methanol fixed for 30 minutes, then methylene blue stained for 30 minutes (Oliver et al, 1989).

Excess stain was washed off with borate buffer and the remaining stain solubilised with acidified ethanol (100 µl/well). The optical density of the wells was read at 630 nm and the results presented in FIG. 1 with the growth response obtained with 10% FBS shown by the dashed line To assess the effect of BMF-1 on cell viability, human keratinocyte cells (HaCat) were plated into 24-place multi-wells to give a monolayer close to confluence and incubated for up to 3 days in complete growth medium. Performed in triplicate, cells were then starved for up to 48 hours and then exposed to concentrations bf BMF-1 (1.0 mg/ml) dissolved in basal medium for between 48 and 72 hours.

Cell monolayers were treated with 4 mM EDTA for 10 minutes and then with trypsin/EDTA (0.125%/0.5 mM) to disperse individual cells. Cells were pelleted, washed in HBSS and to assess cell number, cells were suspended in 450 µl of HBSS and 50 µl trypan blue and counted manually using a haemocytometer. To assess viability, cells were treated with both annexin V/FITC (1 µg/ml) and propidium iodide (PI, 5 µg/ml) in a total volume of 500 µl at 4° C. for 15 minutes (method modified from Van Engeland et al).

Flow cytometry was then used to analyse cells (see Table 2). Cells incubated with annexin/PI were segregated into the following categories; viable cells (negative annexin V staining and negative PI staining), apoptotic cells (positive annexin staining but negative PI staining) and necrotic cells (positive annexin V staining and positive PI staining).

TABLE 2

Effect of BMF-1 (1 mg/ml) on cell growth and survival of cultured keratinocytes (n = 3)

| Treatment | Cell Growth (cells/well × $10^4$) | Annexin/PI (cell viability) | | |
|---|---|---|---|---|
| | | Viable (%) | Apoptotic (%) | Necrotic (%) |
| Basal Medium | 11.0 ± 1.8 | 68.2 ± 2.8 | 21.8 ± 2.5 | 7.4 ± 0.2 |
| BMF-1 | 18.0 ± 1.8 | 76.6 ± 2.0 | 12.5 ± 1.3 | 8.2 ± 0.7 |

Both BMF-1 and BMF-2 stimulated the growth of HaCat cells as shown in FIG. 1. The maximum responses obtained with BMF-1 and BMF-2 were at least comparable to the growth response observed in cells treated with 10% FBS in the same assay (dashed line, FIG. 1). As shown in Table 2, a greater percentage of cells treated with BMF-1 (1 mg/ml) were found to be viable (approximately 12% increase compared to basal medium) and less identified as apoptotic (approximately 43% decrease compared to basal medium). Thus, BMF-1 product stimulates the growth and promotes the survival of cultured human keratinocytes.

EXAMPLE 6

BMF-1 Product Stimulates Collagen Production by Human Skin Fibroblast Cells

Human skin fibroblasts were plated into 6-well plates at a density of about $1 \times 10^5$ cells/well and grown until almost confluent before being starved overnight in basal medium (DMEM and 0.1% FBS). Cells were then exposed to concentrations of BMF-1 (0-2.0 mg/ml) in basal medium for 48 hours. Cell pellets were harvested for hydroxyproline determination as a measurement of collagen content (FIG. 2).

Figure 2:
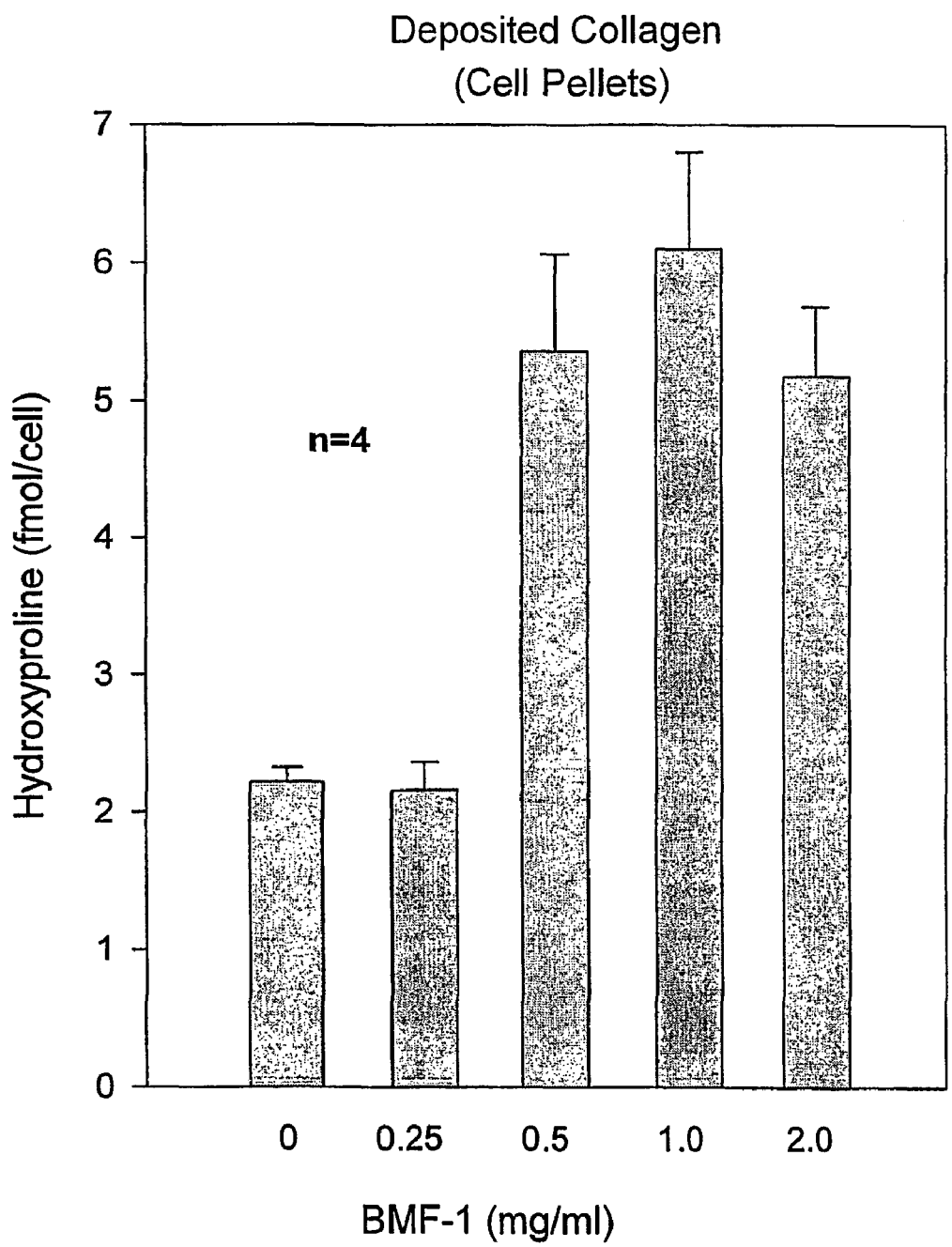
FIG. 2 shows a histogram demonstrating the increase in collagen production in human skin fibroblasts with increasing concentrations of BMF-1. After starving overnight, cells were exposed to BMF-1 for 48 hours. Cells were harvested and the amount of hydroxyproline per cell measured in four replicate samples.

BMF-1 stimulated collagen production by human skin fibroblasts in a dose dependent manner (FIG. 2). The amount of collagen deposited by the cells as extra-cellular matrix was measured in the cell pellets and was found to have increased by up to 3 fold when cells were incubated with BMF-1 compared to basal medium (FIG. 2). Thus BMF-1 stimulates both collagen secretion by human fibroblast cells and deposition of this collagen into the extra-cellular matrix.

EXAMPLE 7

Topically Formulated BMF-1 Penetrates Living Skin

BMF-1 was formulated into four representative topical emulsions on a weight for weight basis with incorporation of up to approximately 20 mg BMF-1 protein per gram of emulsion. Both control emulsion and topically formulated BMF-1 was applied to prepared porcine skin (washed and shaved) at an application rate of approximately 0.05 g/cm². Material was applied by measured syringe (250 µl/5.0 cm² marked area) and rubbed into the skin with a cotton bud until minimal residue was evident on the surface of the skin. After 30 or 90 minutes full thickness 6 mm punch biopsies were harvested from both control and treated areas and snap frozen in Tissue-Tek OCT (optical cutting temperature) compound.

Tissue samples collected in OCT were cut at between 5 and 7 μm using a cryostat and sections fixed in acetone for 20 minutes before being assessed for growth factor staining by immunohistochemistry. Two sections were cut from each section at least 10 μm apart and were rehydrated with phosphate buffered saline (PBS), blocked with 10% skimmed milk powder for 30 minutes at room temperature and washed 2-3 times with PBS. One hundred microliters of the diluted primary antibodies (rabbit anti-TGFβ2 polyclonal antibody 1:200, rabbit anti-IGF-1 polyclonal antibody 1:200) was added to each porcine skin section and left for 1 hour at room temperature before being washed 2-3 times with PBS. One hundred microliters of the diluted secondary antibody (biotinylated anti-rabbit IgG) 1:500 was added to each section and left for a further 1 hour at room temperature before being washed off with 2-3 times PBS and streptavidin-CY3 (1:300) was added to the sections for 40 minutes at room temperature. Finally the sections were washed with PBS and mounted in immu-mount and examined using a fluorescent microscope. Quantitation was performed by capturing 3 complete fields of view of the skin from each of the two sections from each sample. Using SigmaScan software (Jandel Scientific Software), the average intensity of the fluorescence in the epidermis and dermis in each field was determined together with the average background intensity. The final intensity measurement (represented as integrated optical density, IOD) reflects the average intensity in the measured area (epidermis or dermis) minus the background for each field, with up to 6 fields combined to provide the IOD for each sample.

Figure 3A:
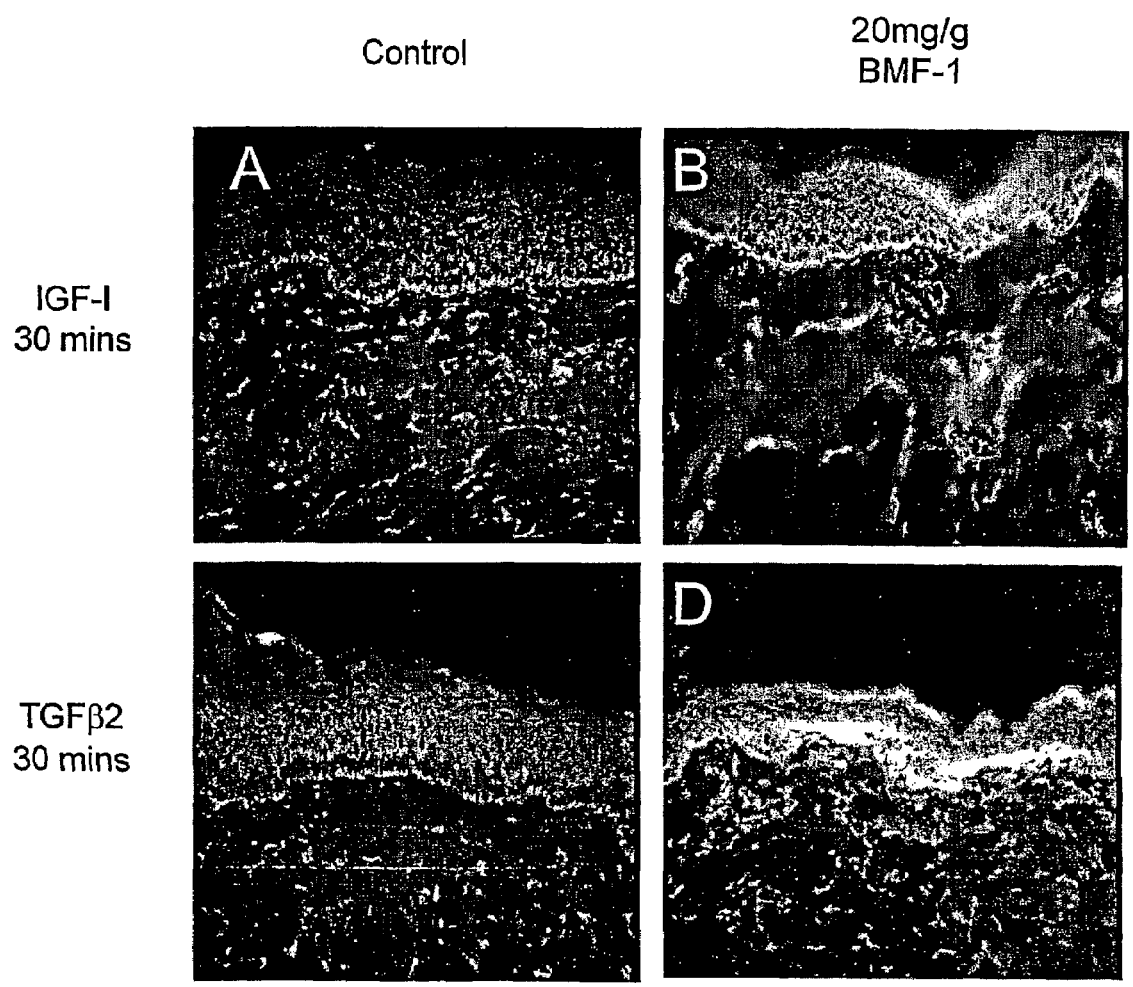
FIG. 3A shows micrographs of porcine skin in cross-section. Topically formulated 20 mg/g BMF-1 or control formulation (vehicle only) was applied to porcine skin, with biopsies being taken after 30 minutes exposure. Sections were prepared and probed using antibodies specific for TGFβ2 or IGF-I. Bound antibody was visualised using fluorescent detection. Panels A and B represent biopsy material stained for the presence of IGF-I (control and treated), while panels C and D represent biopsy material stained for TGFβ2 (control and treated).
Figure 3B:
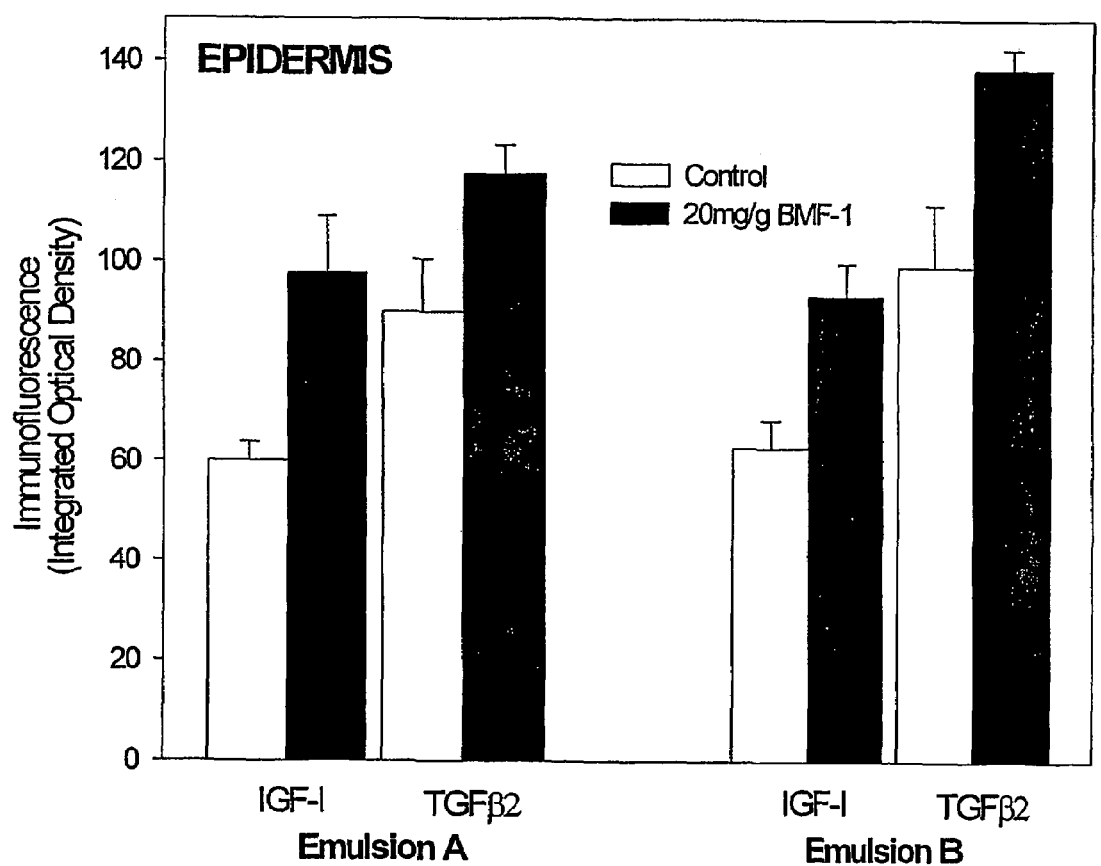
FIG. 3B shows the graphical representation of the measurement of IGF-1 and TGFβ2 immunofluoresence (represented as integrated optical density, IOD) of samples described in 3A with additional samples collected after 90 minutes also analysed. The average intensity of the IGF-I and TGFβ2 immunofluorescence in both the epidermis (3Bi) and dermis (3Bii) of control (open bars) and BMF-1 treated skin samples (closed bars) was obtained by capturing three fields of view from each of two sections from each sample. The results from two topically formulated emulsions containing BMF-1 (A and B) are shown.

IGF-I and TGFβ2 are components of BMF-1 and can be detected in skin using immunohistochemical detection (FIG. 3A). After 30 minutes, the immunohistochemical detection of both IGF-I and TGFβ2 was increased in skin treated with topically formulated BMF-1 preparations (FIG. 3A panels B and D respectively) compared to control skin treated with emulsion only (FIG. 3A panels A and C). FIG. 3B shows the results of the quantitation of the IGF-I and TGFβ2 immunofluorescence observed in the epidermis and dermis of skin treated with two emulsions (A and B) containing 20 mg/g BMF-1 (closed bars) compared to emulsion alone (open bars). Quantitation of IGF-I immunofluorescence was performed on samples taken 30 minutes after the skin was treated with topically formulated BMF-1 whereas quantitation of TGFβ2 immunofluorescence was performed on samples taken 90 minutes after treatment. FIG. 3B confirms the observations shown in FIG. 3A (panels A and B) and demonstrates that IGF-I immunofluorescence was increased in both the epidermis and dermis 30 minutes after the skin was treated with topically formulated BMF-1 preparations. Although TGFβ2 immunofluorescence was found to increase 30 minutes after the skin was treated with topically formulated BMF-1 (FIG. 3A, panels C and D), maximal changes were found to have occurred after 90 minutes. FIG. 3B demonstrates that TGFβ2 immunofluorescence was increased in both the epidermis and dermis after the skin was treated with topically formulated BMF-1. These results indicate that both IGF-I and TGFβ2 have penetrated the skin from the formulation. These studies demonstrate that growth factors contained within the BMF-1 preparations translocate into the skin and are detected in both the epidermal and dermal layers thus confirming the cutaneous availability of formulated BMF-1.

EXAMPLE 8

Topically Formulated BMF-1 Increases Dermal Cellularity in Living Skin

BMF-1 was formulated into 5 base topical emulsions on a weight for weight basis with incorporation of approximately 2 mg and 20 mg BMF-1 per gram of emulsion. Both control emulsion and topically formulated BMF-1 (2 and 20 mg/g) was applied to prepared porcine skin (washed and shaved) at an application rate of approximately 0.05 g/cm². Material was applied by measured syringe (250 μl/5.0 cm² marked area) and rubbed into the skin with a cotton bud until minimal residue was evident on the surface of the skin. Repeated applications were performed at 3 or 4 day intervals for four weeks. Four weeks after the first application, and three days after the last application of topically formulated material, full thickness 6 mm punch biopsies were harvested from both control and treated areas, fixed in 10% formalin and processed for histology.

Wax embedded sections from each biopsy were stained with haematoxylin and eosin and assessed in a blinded fashion by scoring the relative degree of dermal cellularity.

Figure 4:
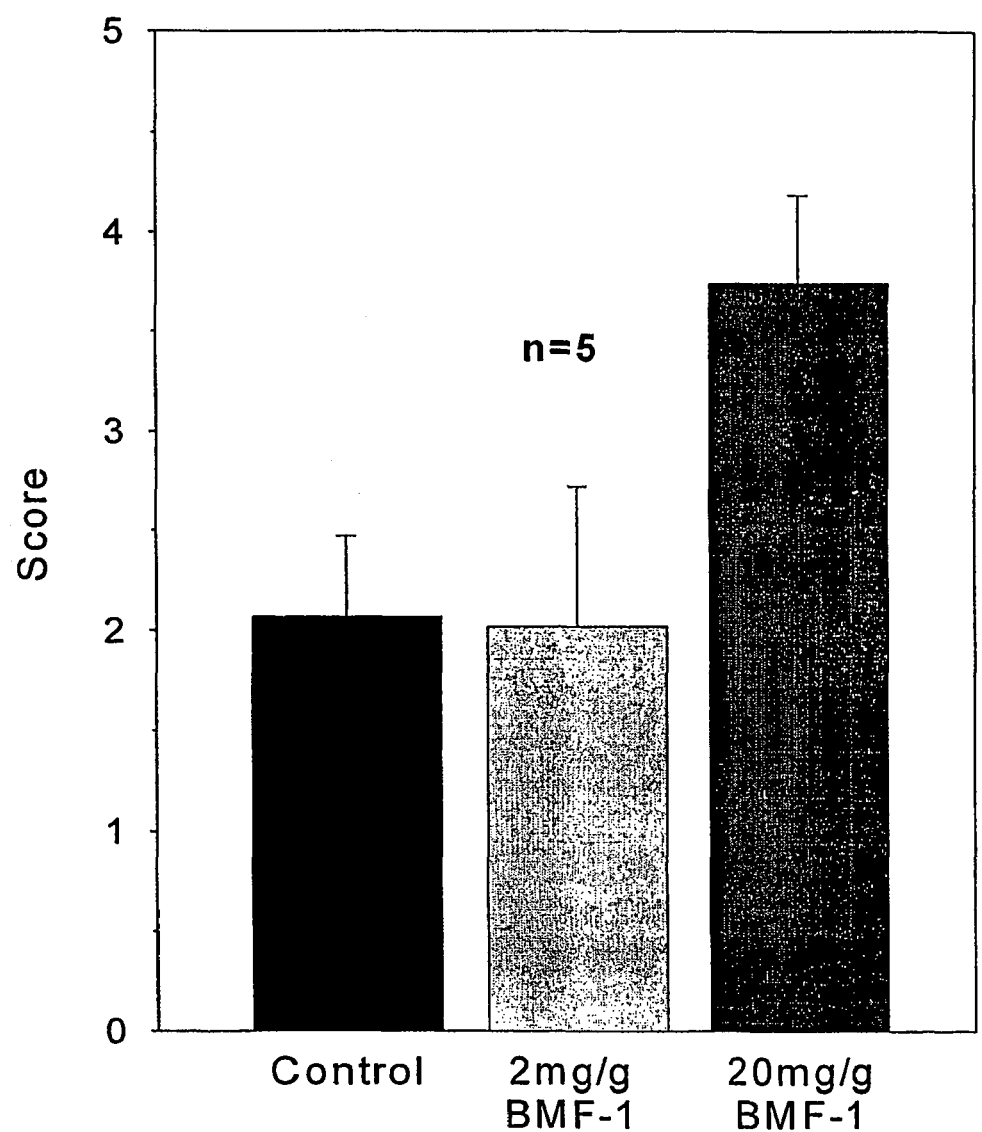
FIG. 4 shows a graphical representation of the dermal cellularity in a skin sample collected after the topical application of 2 mg/g or 20 mg/g of BMF-1. Porcine skin was repeatedly treated for 4 weeks with BMF-1 (high dose or low dose), or control formulation (vehicle only). Biopsies were taken which were analysed microscopically and scored according to the number of fibroblasts. A higher score correlates to higher cellularity.

Following repeated application over four weeks, skin treated with topically formulated BMF-1 (20 mg/g) was observed to have increased dermal cellularity scores compared to controls (FIG. 4), reflecting an increase in the number of fibroblasts in treated skin. As loose connective tissue is more cellular and contains more reticular collagen (type III) than dense connective tissue, an increase in the cellularity score and a increase in type III collagen (Example 9) demonstrates an increase in the deposition of new loose connective tissue in the dermis.

EXAMPLE 9

Topically Formulated BMF-1 Stimulates Collagen Production in Living Skin

BMF-1 was formulated into sorbolene cream on a weight for weight basis with incorporation of approximately 2 and 20 mg BMF-1 per gram of emulsion. Both control cream and topically formulated BMF-1 (2 and 20 mg/g) was applied to prepared porcine skin (washed and shaved) at an application rate of approximately 0.05 g/cm². Material was applied by measured syringe (250 μl/5.0 cm² marked area) and rubbed into the skin of 2 pigs with a cotton bud until minimal residue was evident on the surface of the skin. Repeated applications were performed at 3 or 4 day intervals for two weeks. Two weeks after the first application, and three days after the last application of topically formulated material, full thickness 6 mm punch biopsies were harvested from both control and treated areas and snap frozen in Tissue-Tek OCT compound.

Figure 5:
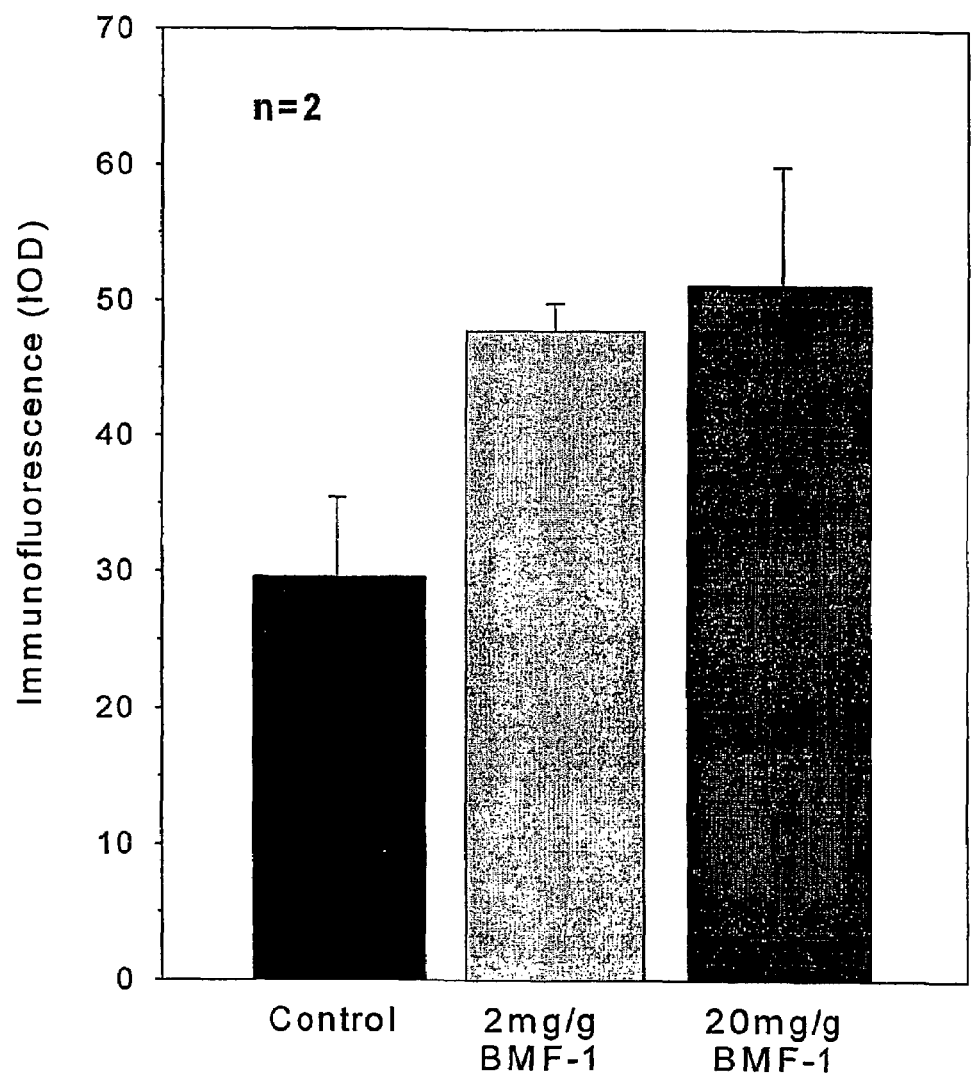
FIG. 5 shows a graphical representation of the production of type III collagen in porcine skin after repeated topical application of 2 mg/g or 20 mg/g of BMF-1 for 2 weeks. Porcine skin was treated with a topical BMF-1 formulation (high dose or low dose), or control formulation (vehicle only). Biopsies were taken and sections stained with an antibody specific for type III collagen. Bound antibody was detected using a fluorescent-tagged secondary antibody, with the fluorescence intensity being quantitated using image analysis software represented by IOD (integrated optical density).

Two 10 μm sections from each tissue sample collected in OCT were cut using a cryostat and sections were fixed in acetone for 25 minutes before being assessed for collagen type III staining by immunohistochemistry. The sections were rehydrated with phosphate buffered saline (PBS), blocked with 10% skimmed milk powder for 40 minutes at room temperature and washed 2-3 times with PBS. One hundred microliters of the diluted primary antibodies (rabbit anti-collagen III polyclonal antibody 1:200) was added to each porcine skin section and left for 1 hour at room temperature before being washed 2-3 times with PBS. One hundred microliters of the diluted secondary antibody (biotinylated anti-rabbit IgG 1:200) was added to each section and left for a further 1 hour at room temperature before being washed off with 2-3 times PBS. Streptavidin-CY3 (1:200) was added to the sections for 40 minutes at room temperature. Finally the sections were washed with PBS and mounted in immu-mount and examined using a fluorescent microscope. Two sections from each tissue sample were analysed using an Olympus-Vanox Photomicroscope and image analysis software. The fluorescence intensity (integrated optical density) was measured in the dermis of each section and normalised using the fluorescence value from a negative control (FIG. 5). Four fields of view were captured from each of the papillary and reticular areas of the dermis. The average intensity values per sample were then combined to provide comparative results.

Following repeated application over two weeks, topically formulated BMF-1 increased the dermal content of collagen type III as shown in FIG. 5. Compared to skin treated with sorbolene cream only, twice weekly exposure to topically formulated BMF (2 and 20 mg/g) increased dermal collagen III immunofluorescence (FIG. 5). These results demonstrate that topically formulated BMF-1 stimulates new collagen deposition (type III collagen) by dermal fibroblasts in skin.

EXAMPLE 10

BMF-1 Product Stimulates Collagen mRNA Synthesis and Inhibits Matrix-metalloproteinase 1 (MMP-1) mRNA Synthesis by Human Skin Fibroblast Cells Human skin fibroblasts were seeded into T75 tissue culture bottles (Cellstar, Greiner GmbH, Frickenhausen) and grown until confluent before being starved overnight in complete growth medium containing 0.1% FBS (basal medium). Cells were then exposed to concentrations of BMF-1 (0-2.0 mg/ml) in basal medium for 48 hours. Cell pellets were harvested for total RNA extraction using a Quickprep RNA extraction kit according to the manufacturers instructions (Amersham Pharmacia Biotech, Piscataway N.J.). The RNA extracted from each bottle was used as a single replicate and gene expression analysed by standard Northern blot procedures of 4 replicate experiments.

Briefly, RNA was quantitated spectrophotometrically and 10 micrograms from each sample was size fractionated by electrophoresis on a 1% agarose-formaldehyde gel, then transferred to a Hybond-N nylon membrane (Amersham, Buckinghamshire, England) and fixed by UV cross-linking (UV Stratalinker 1800, Stratagene, La Jolla, USA). Membranes were probed with antisense riboprobes to human pro-collagen III, pro-collagen I, matrix-metalloproteinase 1 (MMP-1) and GapDH (a constitutively expressed control gene). For the MMP-1 and GapDH hybridisations, pre-hybridisation was carried out at 65° C. for 4 hours in 50% formamide, 5×SSPE, 5× Denhardts, 0.1% SDS and 100 µg/ml sheared salmon sperm DNA. For the collagen hybridisations, ULTRAhyb (Ambion, Austin, Tex.) was used as the hybridisation solution. Riboprobes were generated using either a T7 or SP6 transcription kit (Promega, Madison, USA) and [α-32P]UTP (GeneWorks, Thebarton, Australia), and were used at a final concentration of $10^6$ incorporated counts/ml hybridisation solution. Hybridisation was performed for 16 hours using the conditions described for the prehybridisation. Membranes were washed under high stringency conditions; three times with 3×SSC-0.1% SDS at room temperature, three times with 2×SSC-0.1% SDS at 68° C., followed by two washes with 0.5×SSC-0.1% SDS and 0.1×SSC-0.1% SDS at 68° C. The membranes were exposed to film (Hyperfilm, Amersham, Buckinghamshire, England) at −80° C. for up to 24 hours. For quantitation, membranes were exposed to phosphorimage plates which were scanned by a phosphorimage reader (Fuji BAS, Japan) with the integrated optical density (IOD) of bands measured using Imagemaster VDS software (Pharmacia Biotech, Castle Hill, Australia). To control for the amount of RNA loaded and to ensure changes in mRNA expression reflected specific regulation of the probed gene, the pro-collagen III, I and MMP-1 signal was normalised using the GapDH-IOD from the same sample.

Figure 6A:
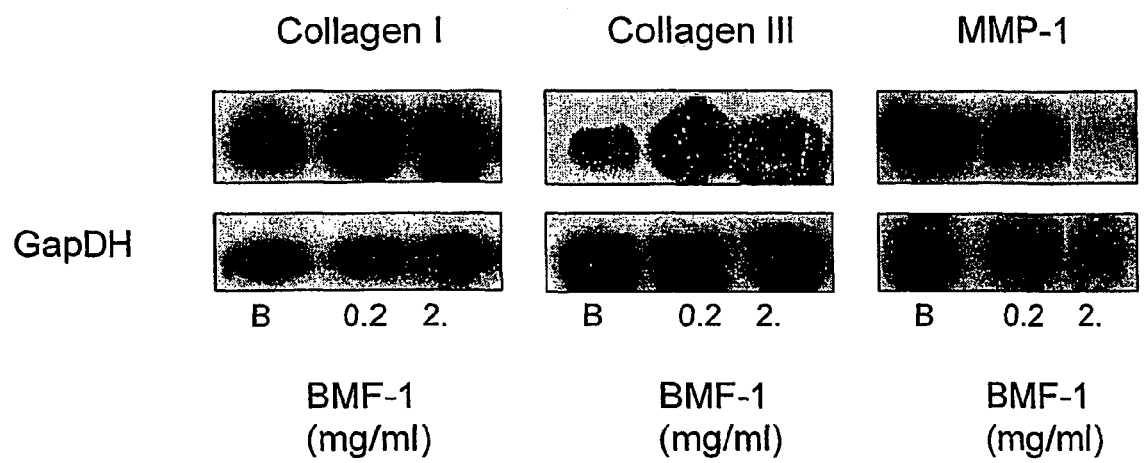
FIG. 6A shows representative autoradiographs of RNA extracted from skin fibroblast cells and probed using Northern blot analysis for collagen I, III, MMP-1 and the control gene GapDH. Cells were cultured for 48 hours in basal media alone (B) or basal media containing 0.2 or 2.0 mg/ml BMF-1.
Figure 6B:
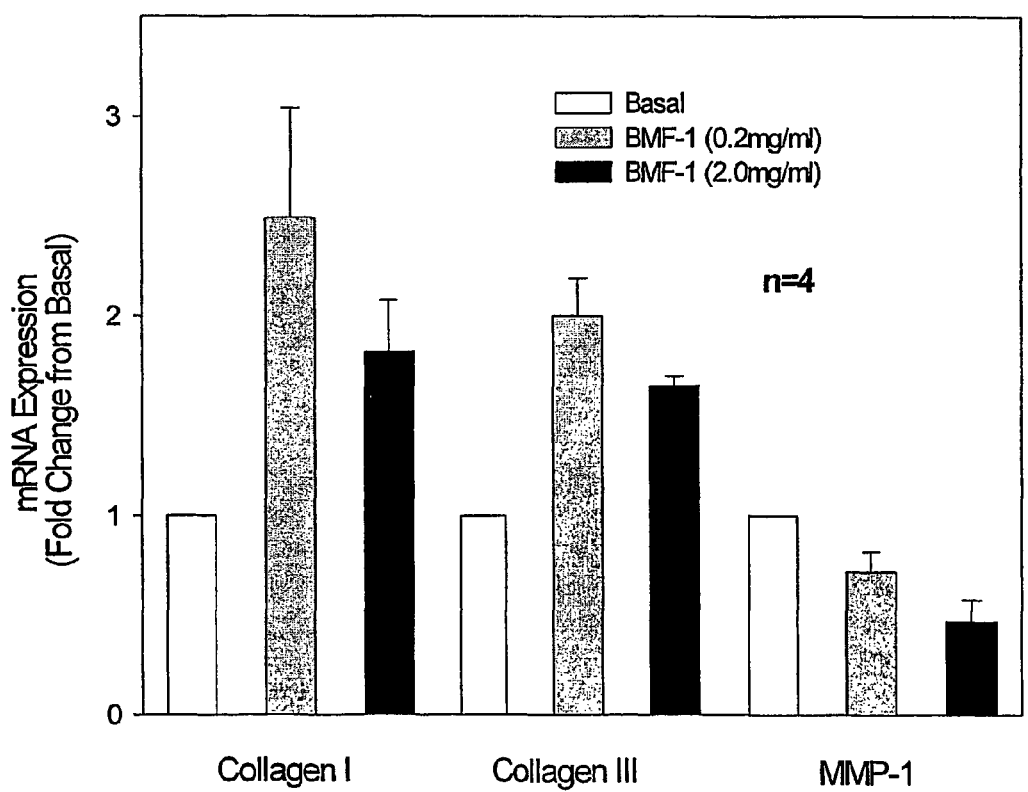
FIG. 6B shows the graphical representation of 4 replicate experiments described in part 6A. Band intensity was measured after exposing probed filters to a phosphorimage plate and the data presented as the fold change of gene expression in RNA from cells treated with 0.2 or 2.0 mg/ml BMF-1 compared to cells cultured under basal conditions. The intensity of each band was normalised to the respective GapDH signal for each sample.

Representative autoradiograms of collagen I, III and MMP-1 probed RNA are shown in FIG. 6A together with the respective GapDH autoradiogram for each sample. FIG. 6B shows the graphical representation of the combined results of 4 replicates for each treatment which are represented as the fold change from the respective RNA expression in cells treated under basal conditions. Treating cells with 0.2 mg/ml BMF-1 induced collagen I and III mRNA expression by at least 2-fold compared to basal conditions. Cells treated with 2.0 mg/ml BMF-1 also showed increased collagen mRNA expression. The effects of BMF-1 is considered to be a direct effect on gene induction and does not just reflect an increase in cell number.

In contrast, BMF-1 had a dose dependent inhibitory effect on the expression of MMP-1 mRNA (FIGS. 6A and 6B). As MMP-1 is an important enzyme in the degradation of the collagen molecule, this result implies that not only does BMF-1 stimulate collagen synthesis, it also inhibits its degradation. As collagen turnover is a dynamic process occurring in skin, the relative effect on synthesis and degradation is an important consideration. The ability of BMF-1 to both stimulate synthesis and inhibit degradation ensures treatment of skin by BMF-1 will ultimately result in an overall net increase in collagen deposition. This is confirmed by the results shown in FIGS. 2 and 5 where the amount of collagen measured was similar in cells (FIG. 2) or skin (FIG. 5) treated with low or high levels of BMF-1. Although the results shown in FIG. 6B indicate that higher doses of BMF-1 do not stimulate as much RNA synthesis as lower doses, the finding that BMF-1 also markedly inhibits the synthesis of the degradative enzyme MMP-1 in a dose dependant manner demonstrates the degradation of collagen by MMP-1 is reduced as the dose of BMF-1 is increased. Moreover, this would result in a similar net balance of collagen deposition by skin fibroblasts at each BMF-1 dose as shown in FIGS. 2 and 5. Thus BMF-1 directly stimulates collagen synthesis by upregulating both collagen I and III gene expression and inhibits its degradation by down-regulating the expression of MMP-1.

EXAMPLE 11

BMF-1 and BMF-2 Product Stimulate Collagen mRNA Synthesis by Human Skin Fibroblast Cells Human skin fibroblasts were seeded into T75 tissue culture bottles (Cellstar, Greiner GmbH, Frickenhausen) and grown until confluent before being starved overnight in complete growth medium containing 0.1% FBS (basal medium). Cells were then exposed to 0.1 mg/ml of BMF-1 or BMF-2 in basal medium for 48 hours. Cell pellets were harvested for total RNA extraction using a Quickprep RNA extraction kit according to the manufacturers instructions (Amersham Pharmacia Biotech, Piscataway N.J.). The RNA extracted from each bottle was used as a single replicate and gene expression analysed by standard Northern blot procedures. Assessment of collagen I and III expression was performed as described in Example 10.

Figure 7A:
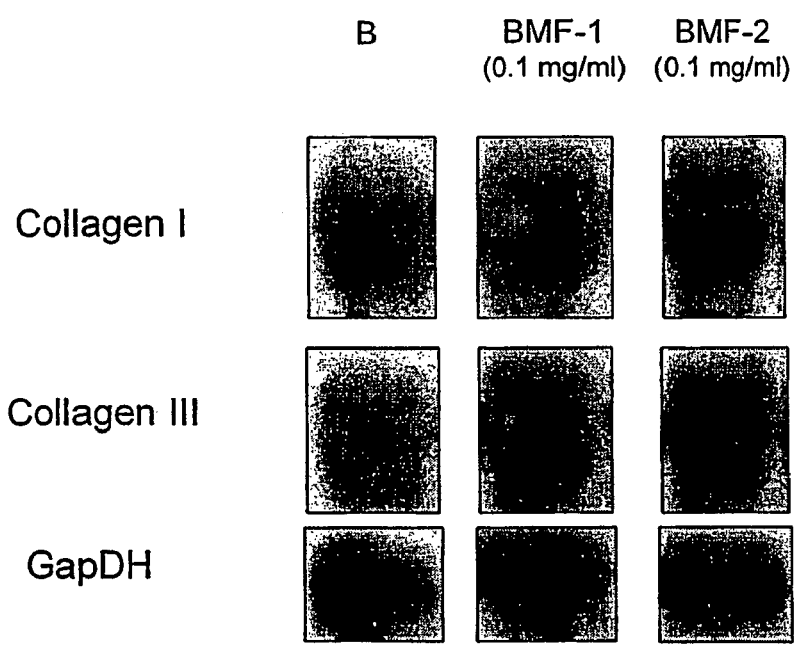
FIG. 7A shows representative autoradiographs of RNA extracted from skin fibroblast cells and probed using Northern blot analysis for collagen I, III and the control gene GapDH. Cells were cultured for 48 hours in basal media alone (B) or basal media containing 0.1 mg/ml BMF-1 or BMF-2.
Figure 7B:
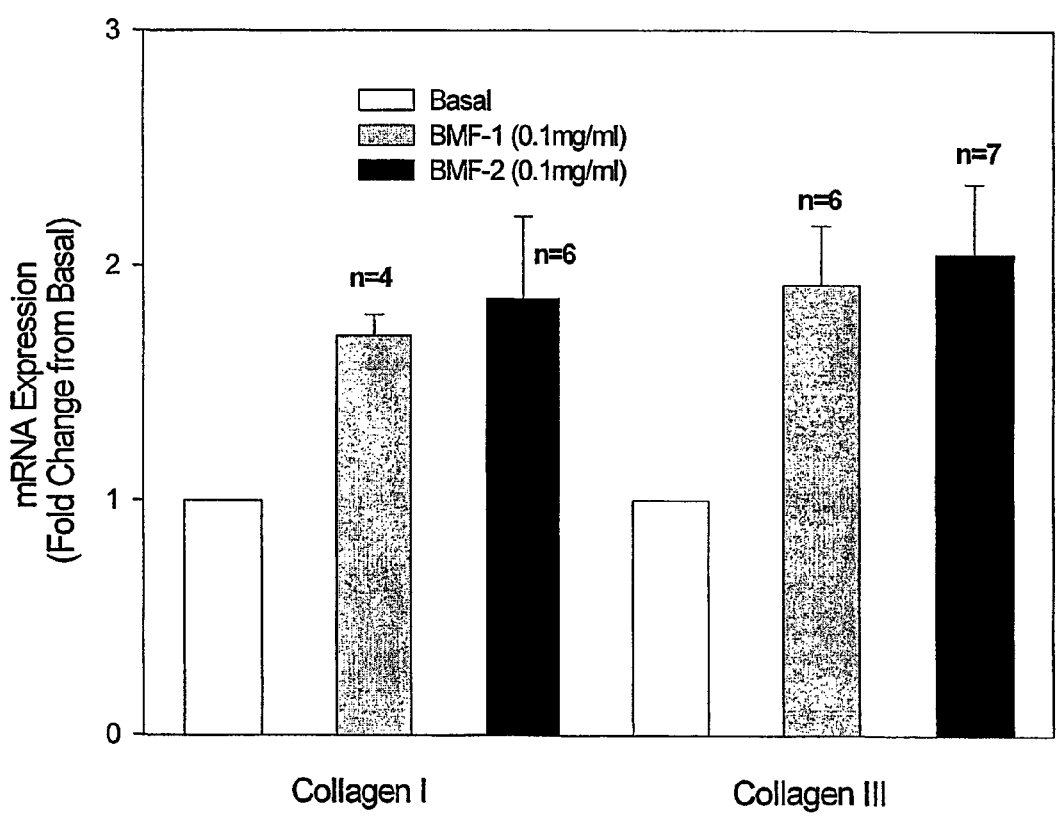
FIG. 7B shows the graphical representation of the combined data from 4-7 replicate experiments described in part A. Band intensity was measured after exposing probed filters to a phosphorimage plate and the data presented as the fold change of gene expression in RNA from cells treated with 0.1 mg/ml BMF-1 or BMF-2 compared to cells cultured under basal conditions. The intensity of each band was normalised to the respective GapDH signal for each sample.

Representative autoradiograms of collagen I and III probed RNA are shown in FIG. 7A together with the respective GapDH autoradiogram for each sample. FIG. 7B shows the combined results of replicates for each treatment which are represented as the fold change from the respective RNA expression in cells treated under basal conditions. Treating cells with both BMF-1 and BMF-2 induced collagen I and III mRNA expression by up to 2-fold compared to basal conditions. Although there was a tendency for BMF-2 to have a greater effect on collagen expression (FIG. 7A), the overall results were comparable (FIG. 7B). As mentioned in Example 10 the stimulation of collagen RNA by BMF-1 and BMF-2 is considered to be the result of a direct effect on gene induction and not just reflect an increase in cell number.

Thus BMF-1 and BMF-2 can directly stimulate collagen synthesis by upregulating both collagen I and III gene expression.

EXAMPLE 12

Methodologies Used to Study the Effectiveness of Basic Milk Factors as a Therapeutic and Preventive Treatment for Skin Damage The invention may be used to treat skin damage caused by UV radiation as a result of sun exposure. The person skilled in the art will readily be able to investigate the claimed invention to treat skin damage caused by sun exposure.

For example, hairless mice exposed daily to a measured Minimal Erythematous Dose (MED) of solar simulated UV irradiation have been widely used as an animal model of accelerated skin damage or photoageing (Maloney et al 1992). This suitable model would be used to induce skin damage followed with the application of formulated BMF-1 or BMF-2 (collectively referred to as "BMF") either alone or in combination with supplementary active ingredients to the damaged skin. The ability of the treatment to repair or renew the skin to a more normal structural and functional state as well as prevent further deterioration of the skin would be determined.

For example, to test the ability of the invention to repair photo-damaged skin, after a period of acclimatisation (approximately one week) Skh-1 hairless mice will be exposed to a Minimal Erythematous Dose (MED) to their whole body of mixed UVA and UVB radiation five times a week. This is the approximate minimum dose which causes the mouse skin to turn pink 24 hours after irradiation. After a period of continued irradiation up to and including 20 weeks, when signs of skin damage are generally detectable, irradiation will be discontinued and the mice will receive a daily topical application of formulated BMF product on the dorsum at a dose rate within the range of 0.001-200 mg/cm$^2$. Preferably, at specified times after the commencement of treatment, animals will be euthanased by the administration of a lethal dose of sodium pentobarbitone. Various methods are known in the art for assessment and characterisation of the effectiveness of the repair of skin damage. For example, the skin is collected for analysis using histological, immunohistochemical and biochemical methods (including hydroxyproline, mRNA and metalloproteinase assays) to determine the ability of BMF containing formulations to repair the UV-damaged skin.

On the basis of the results shown in Examples 2 to 11, the inventors expect that the invention used in this particular model would increase collagen synthesis and deposition and decrease matrix degradation by matrix-metalloproteinases resulting in improved dermal structure and function compared to the skin from matched control treated animals. The inventors also expect that the invention would enhance skin keratinocyte and fibroblast cell proliferation and viability. The inventors also expect that the invention would conceivably reduce wrinkling, skin sagging and other photoageing related changes that occur in the dermis of the skin. Moreover, the inventors expect the invention would improve epidermal structure and viability and thus restore the skin to a normal healthy and youthful appearance.

Further, suitable methods are known in the art to investigate the ability of the invention to prevent skin damage. For example, mice would receive a daily topical application of formulated BMF product on the dorsum at a dose rate within the range 0.001-200 mg/cm$^2$ immediately after being exposed to UV-irradiation (MED). This treatment would be continued for up to 20 weeks and at various times animals would be anaesthetised and then euthanased. Various methods are known in the art for assessment and characterisation of the effectiveness of the prevention of skin damage. Preferably, the skin of BMF treated mice is compared to the skin of control treated mice using standard histological, immunohistochemical and biochemical analysis. On the basis of the results shown in examples 2 to 11, the inventors expect that the invention used in this particular model would reduce the signs of skin damage.

EXAMPLE 13

Methodologies Used to Study the Effectiveness of Basic Milk Factors as a Cosmetic to Enhance the Appearance of Skin The invention may be used as a cosmetic to enhance the appearance and vitality of human skin. The person skilled in the art will readily be able to investigate the claimed invention to improve the cosmetic appearance of human skin.

For example, a number of clinical indices can be used to determine the ability of topically applied cosmetics to enhance skin cosmesis. These include subjective measurements of skin wrinkling, skin appearance and vitality, skin dryness and scaliness, skin sensitivity, skin thickness and skin fragility. More objective measurements can also be taken such as measuring skin thickness by callipers or ultra-sound and measuring skin moisture kinetics by determining epidermal hydration using a corneometer and transepidermal water loss (TEWL, a measurement of transcutaneous water loss) using a tewameter. Similarly skin surface roughness can be measured by taking a natural negative impression of the skin surface using dental impression material and analysing the impressions with a profilometer. Also, the elastic properties of the skin can be assessed using an uniaxial extensometer.

For example, to test the ability of the invention to produce desirable cosmetic effects on human skin, topical application of formulated basic milk factors to the skin, at any site requiring cosmetic improvement, would be performed at a dose rate within the range of 0.001-200 mg/cm$^2$ and at specified application frequencies ranging from daily to weekly to monthly. Preferably, before the commencement of treatment and at specified times after the commencement of treatment, various methods are known in the art for assessment and characterisation of the effectiveness of cosmetics to improve the appearance and vitality of human skin would be applied. For example, measurements of skin wrinkling, skin appearance and vitality, skin dryness and scaliness, skin sensitivity, skin thickness, skin fragility, skin water kinetics and skin elasticity would be used to determine the ability of basic milk factor containing formulations to improve skin cosmesis.

On the basis of the results shown in examples 2 to 11, the inventors expect that the invention would improve the appearance and vitality of skin, thus restoring skin with an aged appearance to a more normal healthy and youthful appearance.

EXAMPLE 14

Methodologies Used to Study the Effectiveness of Basic Milk Factors as a Treatment of Skin Damage Caused by Cutaneous Resurfacing The invention may be used as a treatment of skin damage caused by cutaneous resurfacing. The person skilled in the art will readily be able to investigate the claimed invention to improve the outcome of skin regeneration following cosmetic procedures using high-energy pulsed laser systems and electrosurgical coablation.

For example, cutaneous resurfacing is the cosmetic procedure of choice for the correction of photodamaged skin, photo-induced rhytides, dyschromias, the amelioration of scars and for skin recontouring. Cutaneous resurfacing employs high-energy pulsed lasers of the carbon dioxide ($CO_2$), erbium:yttrium-aluminum-garnet (Er:YAG) or neodymium:yttrium-aluminum-garnet (Nd:YAG) variety or electrosurgical systems for coablation techniques. Despite their effectiveness and utility, cutaneous resurfacing techniques are also associated with some unwanted side effects that occur as a result of the repair processes stimulated by the procedures in damaged skin.

For example, to test the ability of the invention to improve the outcome of human skin regeneration following cosmetic procedures using high-energy pulsed laser systems and electrosurgical coablation topical application of formulated basic milk factors to the skin, at the site of the procedure, would be performed at a dose rate within the range of 0.001-200 mg/cm$^2$ and at specified application frequencies ranging from daily to weekly. Preferably, before the commencement of treatment and at specified times after the commencement of treatment, various methods are known in the art for assessment and characterisation of the effectiveness of treatments to improve the appearance of resurfaced human skin would be applied. For example, measurements of skin wrinkling, skin appearance, skin thickness, skin fragility and skin elasticity would be used together with more specific determinations of erythema, edema, hyperpigmentation, delayed hypopigmentation and hypotrophic scar formation to determine the ability of BMF containing formulations to improve the rejuvenation of skin by cutaneous resurfacing procedures.

On the basis of the results shown in examples 2 to 12, the inventors expect that the invention would improve the cosmetic outcome of skin resurfacing procedures, thus restoring skin more quickly to a more normal healthy and youthful appearance.

It will be apparent to the persons skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Bergfeld W F. Cosmetic use of alpha-hydroxy acids. *Cleveland Clinic J. Med.* 1997 64: 327-329.

Clark R A F. 1995. Wound Repair: Overview and general considerations. The molecular and cellular biology of wound repair, 2$^{nd}$ edition, R. A. F. Clarke, editor. Plenum Press, New York, pp 3.

Gilchrest B A, A review of skin ageing and its medical therapy. *Br. J. Dermatol.* 1996 135: 867-875.

Maloney S J, et al. The hairless mouse model of photoaging: Evaluation of the relationship between dermal elastin, collagen, skin thickness and wrinkles. 1992 *Photochem. and Photobiol.* 56(4):505-511.

Mast B A. 1992. The Skin. In Wound Healing: Biochemical and clinical aspects. Cohen I K, Diegelmann R F, and Linblad W J, editors. Saunders W B, Philadelphia, 346-349.

Oliver M H, Harrison N K, Bishop J E, Cole P J, Laurent G J. A rapid and convenient assay for counting cells cultured in microwell plates: application for assessment of growth factors. *J. Cell. Sci.* 1989 92: 513-518.

Orentreich N, and Orentreich D. S. Dermabrasion. *Clinics in plastic surgery.* 2001 28: 215-230.

Van Engeland M, Ramaekers F. C. S, Schutte B, and Reutelingsperger C. P. M. A novel assay to measure loss of plasma membrane asymmetry during apoptosis of adherent cells in culture. *Cytometry* 1996 24: 131-139.

The invention claimed is:

1. A method for treating skin damage, the method comprising: topically administering to an area of substantially intact skin of a mammal in need thereof an effective amount of a composition for increasing dermal cellularity and/or stimulating collagen production, and/or inhibiting matrix-metalloproteinase 1 production in the skin, the composition comprising a plurality of basic milk factors having basic to approximately neutral isoelectric points, the milk factors being present at concentrations greater than that found in the lactational secretion from which they were derived and separated from the lactational secretion from which they were derived, the plurality of basic milk factors comprising at least one basic milk factor that is insulin-like growth factor 1 (IGF-1) or transforming growth factor β2 (TGF-β2), the basic milk factors having a molecular weight of at least approximately 5,000 Da, wherein upon administration of the composition the at least one basic milk factor having a molecular weight of at least approximately 5000 Da passes through the uppermost layers of skin having barrier function to exert a biological effect on an underlying competent cell.

2. The method according to claim 1 wherein the total concentration of basic milk factors is greater than or equal to about 0.25 mg/mL of composition.

3. The method according to claim 1 wherein the total concentration of basic milk factors is greater than or equal to about 0.5 mg/mL of composition.

4. The method according to claim 1, wherein the composition is obtained by a method comprising adsorbing the milk factors to a cation exchange matrix, eluting the milk factors from the matrix, acidifying and concentrating the eluate.

5. The method according to claim 1, wherein the method stimulates production of collagen in the substantially intact skin.

6. The method according to claim 1, wherein the method increases dermal cellularity in the substantially intact skin.

7. The method according to claim 1, wherein the method inhibits production of matrix metalloproteinase 1 in the substantially intact skin.

* * * * *